United States Patent [19]

Marsoner et al.

[11] Patent Number: 5,017,339
[45] Date of Patent: May 21, 1991

[54] APPARATUS FOR MEASURING THE COMPONENTS OF A SAMPLE

[75] Inventors: Hermann Marsoner, Steinberg; Fritz Fischer; Erich Kleinhappl, both of Graz, all of Austria

[73] Assignee: AVL AG, Schaffhausen, Switzerland

[21] Appl. No.: 329,837

[22] Filed: Mar. 28, 1989

[30] Foreign Application Priority Data

Mar. 28, 1988 [AT] Austria .................................. 830/88

[51] Int. Cl.$^5$ ...................... G01N 27/00; G01N 31/00
[52] U.S. Cl. .................. 422/82.04; 422/81; 204/403; 204/409; 204/411
[58] Field of Search ............ 422/81, 82.03, 82.04; 436/52, 60, 150, 151; 204/403, 409, 411

[56] References Cited

U.S. PATENT DOCUMENTS 4,409,088 10/1983 Kanno et al. .................. 204/402
4,520,108 5/1985 Yoshida et al. .................. 436/52
4,535,786 8/1985 Kater .................. 128/760

Primary Examiner—David L. Lacey
Assistant Examiner—David Redding
Attorney, Agent, or Firm—Watson, Cole, Grindle & Watson

[57] ABSTRACT

An apparatus for measuring the properties of a sample includes a sensor block with at least one sensor module whose housing contains a measuring chamber in contact with a sensor, the housing of the sensor module M including a mixing chamber for indirect measurement of a sample property, which chamber is placed upstream of the measuring chamber, and is connected with a sample channel and a reagent channel. Due to the modular design of the sensor block, the sample and reagent paths in the sensor block or sensor module may be kept short; along with the compact arrangement of mixing chamber and measuring chamber this permits the required sample and reagent volumes to be kept to a minimum.

16 Claims, 3 Drawing Sheets

APPARATUS FOR MEASURING THE COMPONENTS OF A SAMPLE

BACKGROUND OF THE INVENTION

This invention relates to an apparatus for measuring the components of a sample, which includes a sensor block with at least one sensor module, whose housing contains a measuring chamber in contact with the sensor.

DESCRIPTION OF THE PRIOR ART

A device of the above kind is disclosed in Austrian Pat. No. 381 794, for example; in the embodiment presented there it comprises three sensor modules combined in a sensor block, which are traversed by a sample passage configured as a central capillary bore.

Suitable sensor modules are ion-sensitive capillary electrodes (cf. Austrian Pat. No. 363 263), which are pressed against a stationary end piece of the sensor block by means of a tightening mechanism.

The sensor modules described in the above publications are suited only for direct measurement of a particular sample component, whereas an indirect measurement is not possible with the use of the known device.

Indirect measurement in this context implies that the sample is modified before measurement of a specific sample component, i.e., by mixing it with a reagent at a defined ratio by volume, the desired quantity being measured indirectly, for instance via a reaction product developing in proportion to the quantity of the sample component of interest, to which product the inserted sensor responds. Direct measurement therefore implies that the inserted sensor is capable of directly transforming the sample component of interest into an evaluable signal by means of a specific measuring element, without modification or alteration of the sample material.

In European patent application No. 0 163 976 a measuring device similar to that of Austrian Pat. No. 381 794 is described, the main difference being that the sample and the calibrating media are drawn in from opposite ends of the sensor module, causing the reference electrode positioned at one end of the sensor module to contaminate the medium to be measured if a medium is drawn from this end. This kind of device also does not contain a sensor module for indirect measurement.

Conventional apparatus and methods for indirect measurement of the components of a sample are fairly complex from a technical and operating point of view, with regard to sample preparation preceding the measuring process itself. They make it difficult to maintain optimum reproducible parameters or conditions of measurement. Besides, they necessitate comparatively large sample volumes for the individual steps of mixing and reacting, which is of disadvantage, especially in areas such as medical analysis, where only small sample amounts are available.

SUMMARY OF THE INVENTION

It is the object of this invention to propose a measuring apparatus with which reproducible indirect measurements of the components of a sample may be obtained in a technically simple manner, and for which small sample and reagent volumes are sufficient in order to obtain a measurement value.

In the invention this object is achieved by placing a mixing chamber connected with a sample channel and a reagent channel in front of the measuring chamber in the housing of the sensor module, for the purpose of indirect measurement of a sample component. Due to the modular design of the sensor block, the sample and reagent paths in the sensor block or sensor module may be kept short, which, together with the compact arrangement of the mixing and measuring chambers, will permit the use of minute sample and reagent volumes. Depending on the types of sample components to be measured, sensors embodying different measuring principles may be inserted into the sensor module. Upon mixing the sample with one or several reagents simultaneously entered through the reagent channel, a reaction will take place and a reaction product suitable for measurement by the sensor will be obtained.

In a further development of the invention a magnetic stirrer is provided in the mixing chamber of the sensor module, which stirrer may be actuated by magnetic conductors connected with a magnetizing coil.

This variant provides that the housing of the sensor module should have a removable mixer part containing the mixing chamber and the magnetic stirrer, with connections for the sample channel, the reagent channel and the channel into the mixing chamber, and that two magnetic conductors be provided, which are positioned in the mixer part and directed towards the mixing chamber. By guiding the magnetic force actuating the magnetic stirrer towards the mixing chamber by means of magnetic conductors, the mixer part containing the mixing chamber may be given a most compact design. It may be removed easily for cleaning or replacement of worn-out components, or for total replacement of the entire part, after the sensor module has been removed from the sensor block.

For greater ease of replacement of one or several sensor modules in a sensor assembly the invention provides that the sensor module be pressed against a stationary end piece of the sensor block by means of a tightening mechanism in a known manner, the sample channel of the sensor module being sealingly connectable to a channel section in the end piece, and that the magnetizing coil be located in a pressure element of the tightening mechanism, which may be pressed against the mixer part by spring elements, and that magnetic conductors extending from the magnetizing coil be located in the pressure element, which are brought into contact with the magnetic conductors in the mixer part.

In the invention replacement of the mixer part is facilitated by providing the housing of the sensor module with a spring-loaded arresting knob on the side facing the base plate, by which knob the removable mixer part is sealingly pressed against the measuring chamber upon its insertion into the housing.

The mixer part of the sensor module is provided with a locking part sealing the mixing chamber, whose central bore is sealed against the channel towards the measuring chamber, which locking part has a cylindrical stub projecting into the mixing chamber. This locking part facilitates production of the mixing part and in its built-in state has both sealing and protective functions for the mixing chamber.

The sensor may also project into a part of the mixing chamber configured as a measuring chamber. This configuration may be employed if the reagents used do not affect the sensor or sensor membrane. In this instance care should be taken to prevent any mechanical damage of the sensor by a magnetic stirrer.

Particularly homogeneous mixtures and rapid reactions are obtained if the reagent channel opens into the sample channel immediately in front of the mixing chamber in flowing direction of the sample.

A preferred variant of the invention provides that at least one sensor module of a known type for direct measurement of sample components be inserted between the stationary end piece of the sensor block and the sensor module for indirect measurement of sample components, one of the connections of the above sensor module for direct measurement being sealingly connected to the sample channel of the adjacent sensor module, while the other one is sealingly connected to the section of the channel in the end piece. For direct measurement of sample components the use of sensors as described in detail in Austrian Pat. Nos. 363 263, 379 318 and 380 741 is recommended. For instance, the ion-sensitive membrane electrode for measuring the ionic concentration of a sample according to Austrian Pat. No. 379 318, and the ionsensitive capillary electrode according to Austrian Pat. No. 363 263 mentioned above, have sample passages traversing the sensor module in axial direction, making these sensors particularly suited for being used side by side in a sensor block together with the sensor module for indirect measurement specified by the invention. In this way a measuring apparatus to be described in more detail below may be obtained for joint indirect and direct measurement of the components of a sample.

For the use of at least one electrochemical electrode in one of the sensor modules the invention further proposes that the section of the channel in the end piece be made of electrically conductive material and be connected to an electric lead. This will permit the sample to be held at a certain potential, for instance ground. It will also be possible to insert suitable optical sensors or optodes into the individual sensor modules, in which case no ground or reference electrodes are needed.

A further development of the invention provides that the sensor module have a $CO_2$ sensor for measuring the total carbon dioxide in a sample of blood serum. In a sample of blood serum the total carbon dioxide consists of dissolved $CO_2$ and the bicarbonate content of the sample. The carbon dioxide chemically bound in the bicarbonate is separated out by the addition of an acid reagent to the mixture. This results in a high partial pressure of the molecularly dissolved carbon dioxide, which is measured by the $CO_2$ sensor. The same principle may be applied to many other reactions, e.g., for measuring the total content of calcium ions. In case of a gaseous medium to be measured a vertical arrangement of the measuring chamber above the mixing chamber may be of advantage.

In a measuring apparatus comprising a feeder device for sample and standard media connected with the sample channel of the sensor module, vessels for the standard media and a feed pump for transport of the individual media, the proposal is put forward by the invention that the tube running from a reagent vessel to the reagent channel of the sensor module, and the tube running from the feeder device to the sample channel of the sensor module both be acted upon by a joint peristaltic pump. Based on the measuring device disclosed in Austrian Pat. No. 381 794 the above improvements will permit a measuring apparatus to be used for joint direct and indirect measurement of the components of a sample. By positioning the peristaltic pump handling both sample and reagent solutions in front of the sensor block, a constant mixing ratio of the two media is obtained, the mixing ratio between sample and reagent required for the reaction process being defined by the ratio of the cross-sections of the tubes leading to the reagent channel and the sample channel.

In a preferred version the reagent is used as a reference medium at the same time, if at least one electrochemical sensor is used and if a reference electrode is located in one of the sensor modules in the reagent channel, preferably outside of the sensor block.

DESCRIPTION OF THE DRAWING

Following is a more detailed description of the invention as illustrated by the attached drawing, in which FIG. 1 gives a schematic view of an apparatus according to the invention.

DETAILED DESCRIPTION OF THE PREFERRED EMBODIMENT

Figure 1:
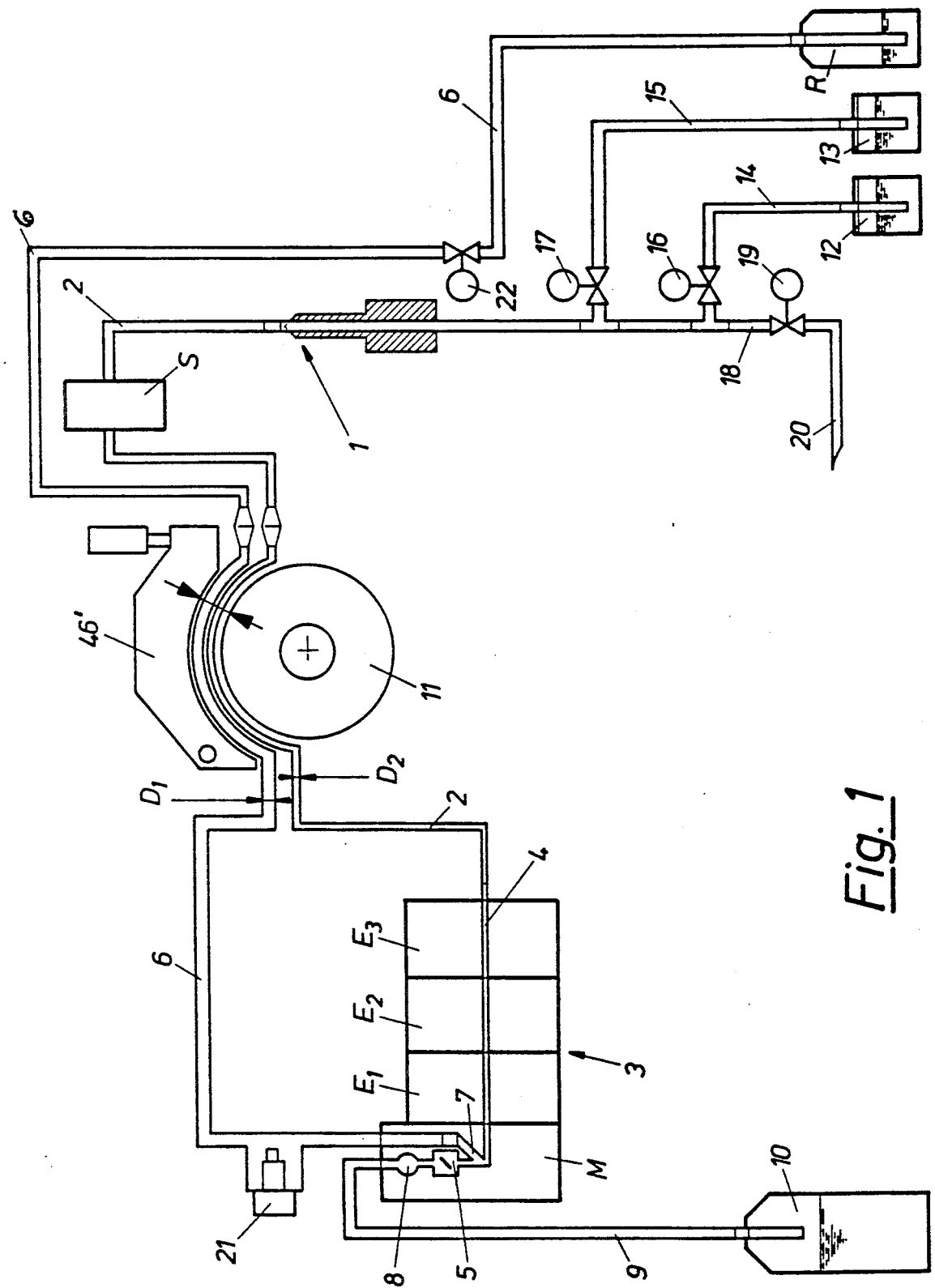

FIG. 1 shows an apparatus for measuring the components of a sample, comprising a sample feeder device 1 as disclosed in Austrian Pat. No. 381 794 above, which may be switched from an initial position as shown to a feed position in order to enter a sample into the path of analysis. The sample feeder device 1 is connected to a sensor block 3 by means of a tube 2 containing a photoelectric barrier S for checking the passage of the sample or standard medium. In the embodiment shown the sensor block 3 has three sensor modules $E_1$, $E_2$, $E_3$ for direct measurement and one sensor module M for indirect measurement of sample components, which are connected with one another by a sample channel 4 configured as a central capillary bore, and are exposed to the sample flowing through this channel.

In the embodiment presented here the sensor modules $E_1$, $E_2$, $E_3$ and M have electrochemical sensors or electrodes (for a detailed view cf. FIG. 2); the invention would also permit the use of optical sensors, however. The sensors are provided with signal leads (not shown here in detail) delivering for evaluation measuring signals proportional to the quantity to be measured.

From a reagent vessel R the reagent required for the reaction in the mixing chamber 5 of the sensor module M, by which the direct measurement of the sample components is effected, is carried to the reagent channel 7 of the sensor module M via a tube 6, which may be opened and closed by means of a control valve 22. After the sample and the reagent have been mixed, the mixture enters the measuring chamber 8 and is drained through a pipe 9 into a waste container 10. A peristaltic pump 11, which is located in front of the sensor block 3 in the flow direction of the media, and is provided with a removable bracket 46', acts upon both the tube 6 for the reagent and the tube 2 for the sample medium, the ratio of the cross-sections $D_1$, $D_2$ of the tubes 2, 6 determining the mixing ratio of the sample/reagent mixture.

In addition to the reagent vessel R two further vessels 12, 13 are provided in the measuring apparatus, containing different standard solutions, etc., which are connected to a feed line 18 into the sample feeder device 1 by tubes 14, 15 and control valves 16, 17. The feed line 18 has an opening 20 for drawing air, which may be closed by another control valve 19.

If an electrochemical electrode is used in at least one of the sensor modules $E_1$, $E_2$, $E_3$ or M, the corresponding reference electrode 21 may be inserted outside of the sensor block 3 directly into the reagent channel 7 or, as shown in FIG. 1, into the tube 6 carrying the reagent solution. The reagent thus is employed as a reference solution at the same time.

Figure 2:
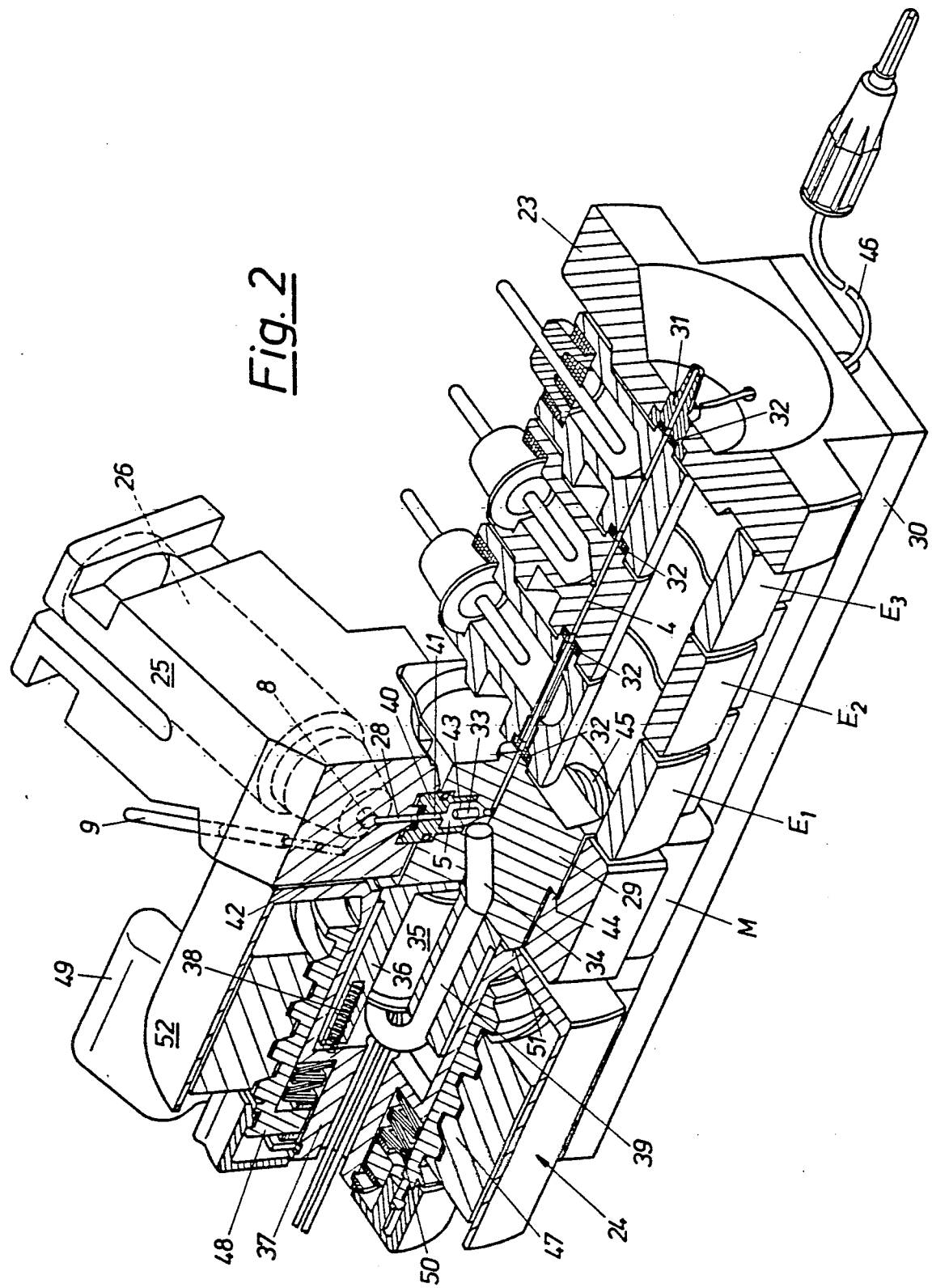
FIG. 2 is a perspective view of a partially sectioned sensor block of the apparatus.

A combination of a sensor module M designed for indirect measurement and sensor modules $E_1$, $E_2$, $E_3$ designed for direct measurement is shown in the detailed view of a sensor block 3 in FIG. 2. Between a stationary end piece 23 and an axially movable tightening mechanism 24 are located the known sensor modules $E_1$–$E_3$ and a sensor module M for indirect measurement of a sample component, which is to be described in more detail below. The end piece 23 and the tightening mechanism 24 are permanently screw-fastened to a base plate 30. In a modified version other sensor assemblies are possible, for instance, with the sensor module M directly pressing against the end piece 23. The end piece 23 has a channel section 31, with which the sample channel 4 of the respective sensor module adjacent to the end bearing is connected via a sealing element 32. The channel section 31 is made of electrically conductive material and is connected to an electric lead 46. By means of this lead the channel section 31 may be connected to a defined electric potential. As the sample flows through the channel section 31 it may thus be held at a given electric potential. As a rule this will be used for grounding of the sample.

Figure 3:
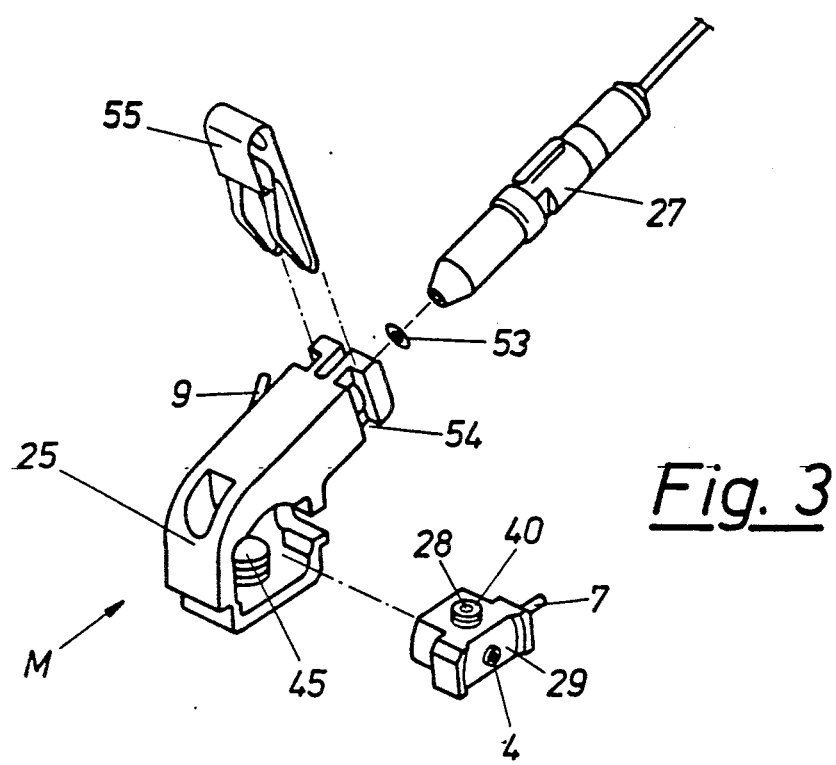
FIGS. 3 and 4 show details of a sensor module from the sensor block presented in FIG. 2.

The sensor module M has a housing 25 with an opening 26 for insertion of an electrochemical sensor 27 as shown in FIG. 3. The membrane of the inserted sensor 27 forms a wall of the measuring chamber 8 from which a channel 28 leads to the mixing chamber 5 located in a removable mixer part 29. The mixing chamber 5 contains a magnetic stirrer 33, which is actuated by (non-permanently magnetic) magnetic conductors 34 located in the mixer part 29.

The magnetizing coil 35 supplying the magnetic conductors 34 is located in a pressure element 36. The pressure element 36 is situated in a recess of the pressure body 37 which is part of the tightening mechanism 24, and is pressed against the removable mixer part 29 by means of a spring element 38 supported by the pressure body 37, such that magnetic conductors 39 departing from the magnetizing coil 35 and situated in the pressure element 36 are brought into contact with those in the mixer part 29 in the section of the drawing shown here only one conductor of either pair of non-permanently magnetic ferromagnetic conductors 34, 39 is visible).

The mixer part 29 is provided with a locking part 40 sealing the mixing chamber 5 in the direction of the measuring chamber 8, whose central bore 41 is sealed against the channel 28 towards the measuring chamber 8 by means of a seal 42. A hollow cylindrical stub 43 of the locking part 40 projecting into the mixing chamber 5 protects the walls of the mixing chamber from wear caused by the magnetic stirrer. In order to remove the mixer part 29 from the housing 25, it must be pressed downward against the force of a spring-loaded arresting knob 45, whereupon it may be removed from the housing 25 in the direction of the axis of the sample channel 4, and replaced, as shown in detail in FIG. 3. After a new mixer part has been inserted, it is sealingly pressed against the measuring chamber by the spring-loaded arresting knob 45 once it rests against a step 44 in the housing 25.

As soon as the magnetizing coil 35 is excited by an alternating voltage of suitable frequency and the ensuing magnetic field is propagated into the area of the mixing chamber 5 via the magnetic conductors 39, 34, the magnetic stirrer 33 starts wobbling. From the rear side of the mixer part 29 (with reference to the view given in FIG. 3) the reagent channel 7 goes into the mixer part and opens into the sample channel 4 immediately in front of the mixing chamber. Through the channel 7 a reagent is added to the sample, with which it is thoroughly mixed in the mixing chamber. From this mixing process and the subsequent reaction a reaction product is obtained whose proportion to the sample component to be measured is known and which may be measured by the sensor 27 projecting into the measuring chamber 5. Draining of the sample/reagent mixture is effected through pipe 9 into the waste container 10 (FIG. 1).

The tightening mechanism 24 presses the sensor modules $E_1$, $E_2$, $E_3$ and M together in axial direction, such that the sealing elements 32 along the sample channel 4 are brought into sealing contact. The axial shift of the pressure body 37 is effected by means of a stationary thread 47 mounted on the base plate 30 and a movable threaded bolt 48, the latter 48 being turned by the lever 49 and acting upon the pressure body 37 via pressure springs 50. In the position of the lever 49 presented here the pressure body 37 is axially preloaded against the force of the springs 50, pressing together the sensor modules via the seat 51, or rather, pressing the mixer part 29 against the adjacent sensor module $E_1$. Part of the pressure body 37 is configured as a cover 52 of the tightening mechanism.

FIG. 3 shows the individual parts of the sensor module M removed from the sensor block, which module M comprises a housing 25, into which may be inserted a mixer part 29 as well as the sensor 27 used for the purpose of measurement, which is sealed inside the housing against the measuring chamber by the gasket 53 and is held in place by a clip 55 engaging in a groove 54 in the housing 25. The mixer part 29 shows the sample channel 4, the reagent channel 7, and the channel 28 located in the locking part 40. As described above, the mixer part 29 may be inserted into the housing of the sensor module M from the side facing the viewer, and is arrested by the spring-loaded arresting knob 45.

Figure 4:
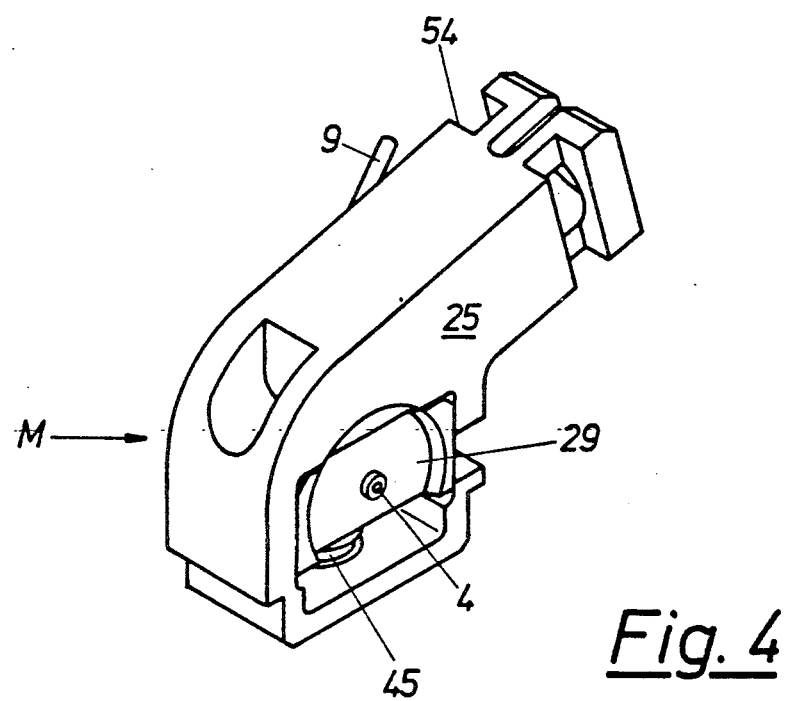

FIG. 4 shows the sensor module M with the mixer part 29 in place.

We claim:

1. An apparatus for measuring chemical and physicochemical properties of a sample, comprising
   a sensor block with at least one sensor module for indirect measurement of at least one sample property, said sensor module comprising a housing which contains a sample channel and a measuring chamber which is contacted by a sensor,
   a removable mixer part containing a mixing chamber with a magnetic stirrer and having at least one connection for said sample and a reagent medium and a channel leading into said measuring chamber, said mixer part being positionable in said housing of said sensor module, and
   two magnetic conductors positioned in said mixer part which are connectable with a magnetizing coil and are directed towards said magnetic stirrer in said mixing chamber, wherein for indirect measurement of at least one of said sample properties said sample and said reagent medium are mixed in said mixing chamber.

2. An apparatus according to claim 1, further including a tightening mechanism positioned so as to press said sensor module against a stationary end piece of said sensor block, said sample channel of said sensor module being sealingly connectable to a channel section in said end piece, and wherein said magnetizing coil is located in a pressure element of said tightening mechanism, spring elements positioned so as to press said pressure element against said movable mixer part of said sensor module, and wherein magnetic conductors extending from said magnetizing coil are located in said pressure element and can contact said magnetic conductors in said mixer part.

3. An apparatus according to claim 1, wherein said housing of said sensor module is provided with a spring-loaded arresting knob positioned and arranged so as to sealingly press said removable mixer part towards said measuring chamber.

4. An apparatus according to claim 1, wherein said mixer part is provided with a locking part sealing said mixing chamber, a central bore of said locking part is sealed against said channel towards said measuring chamber, and wherein said locking part has a hollow cylindrical stub projecting into said mixing chamber.

5. An apparatus according to claim 1, further comprising a reagent channel which opens into said sample channel immediately in front of said mixing chamber.

6. An apparatus according to claim 1, comprising a feeder device for sample and standard media connected with said sample channel of said sensor module, vessels for standard media and a feed pump for transport of said sample and standard media, wherein a tube running from a reagent vessel to said reagent connection of said sensor module, and a tube running from said feeder device to said sample channel of said sensor module are both acted upon by a joint peristaltic pump.

7. An apparatus according to claim 1, wherein said sensor module contains a $CO_2$ sensor for measuring the total carbon dioxide in a sample of blood serum.

8. An apparatus according to claim 2, wherein at least one sensor module for direct measurement of at least one of said sample properties is positioned between said stationary end piece of said sensor block and said sensor module for indirect measurement of at least one of said sample properties and has two connections, one of said connections of said sensor module for direct measurement being sealingly connected to said sample channel of an adjacent sensor module, the other of said connections is sealingly connected to said channel section in said end piece.

9. An apparatus according to claim 2, comprising at least one electrochemical sensor in one of said sensor modules, wherein said channel section in said end piece is made of electrically conductive material and is connected to an electric lead.

10. An apparatus according to claim 8, comprising a feeder device for sample and standard media connected with said channel section of said end piece, vessels for standard media and a feed pump for transport of said sample and standard media, wherein a tube running from a reagent vessel to said reagent connection of said sensor module for indirect measurement, and a tube running from said feeder device to said channel section of said end piece are both acted upon by a joint peristaltic pump.

11. An apparatus according to claim 10, wherein said tube extending from said reagent vessel to said reagent connection and said tube extending from said feeder device to said sample channel have differ cross-sections.

12. An apparatus according to claim 10, including at least one electrochemical sensor positioned in one of said sensor modules and wherein a reference electrode is located in said reagent tube.

13. An apparatus according to claim 12, wherein said reference electrode is located, outside of said sensor block.

14. An apparatus according to claim 6, wherein said tube extending from said reagent vessel to said reagent connection and said tube extending from said feeder device to said sample channel have different cross-sections.

15. An apparatus according to claim 6, including at least one electrochemical sensor positioned in one of said said sensor modules and wherein a reference electrode is located in said reagent tube.

16. An apparatus according to claim 15, wherein said reference electrode is positioned outside of said sensor block.

* * * * *